United States Patent

Cragg et al.

[11] Patent Number: 5,868,762
[45] Date of Patent: Feb. 9, 1999

[54] PERCUTANEOUS HEMOSTATIC SUTURING DEVICE AND METHOD

[75] Inventors: Andrew H. Cragg, Edina, Minn.; Rodney Brenneman, San Juan Capistrano, Calif.

[73] Assignee: Sub-Q, Inc., Del.

[21] Appl. No.: 937,939

[22] Filed: Sep. 25, 1997

[51] Int. Cl.$^6$ ................................................. A61B 17/04
[52] U.S. Cl. ........................... 606/144; 606/148; 606/232
[58] Field of Search .................................. 606/144–148, 606/213, 232

[56] References Cited

U.S. PATENT DOCUMENTS

| | | |
|---|---|---|
| 4,619,261 | 10/1986 | Guerriero . |
| 4,852,568 | 8/1989 | Kensey . |
| 4,890,612 | 1/1990 | Kensey ..................................... 606/213 |
| 4,929,246 | 5/1990 | Sinofsky ....................................... 606/8 |
| 5,021,059 | 6/1991 | Kensey et al. ........................... 606/213 |
| 5,061,274 | 10/1991 | Kensey ..................................... 606/213 |
| 5,221,259 | 6/1993 | Weldon et al. ............................ 604/96 |
| 5,275,616 | 1/1994 | Fowler ..................................... 606/213 |
| 5,342,388 | 8/1994 | Toller ....................................... 606/261 |
| 5,364,408 | 11/1994 | Gordon .................................... 606/144 |
| 5,383,899 | 1/1995 | Hammerslag ............................ 606/214 |
| 5,391,183 | 2/1995 | Janzen et al. ............................ 606/213 |
| 5,417,699 | 5/1995 | Klein et al. .............................. 606/144 |
| 5,419,765 | 5/1995 | Weldon et al. ............................ 604/96 |
| 5,462,561 | 10/1995 | Voda ........................................ 606/144 |
| 5,486,195 | 1/1996 | Myers et al. ............................. 606/213 |
| 5,527,322 | 6/1996 | Klein et al. .............................. 606/144 |
| 5,573,540 | 11/1996 | Youn ........................................ 606/144 |
| 5,613,975 | 3/1997 | Christy .................................... 606/144 |
| 5,632,752 | 5/1997 | Buelna ..................................... 606/144 |
| 5,720,757 | 2/1998 | Hathaway et al. ....................... 606/144 |
| 5,810,850 | 9/1998 | Hathaway et al. ....................... 606/144 |

FOREIGN PATENT DOCUMENTS

95/32671  12/1995  WIPO ............................ A61B 17/12

*Primary Examiner*—Gary Jackson
*Attorney, Agent, or Firm*—Burns, Doane, Swecker & Mathis LLP

[57] ABSTRACT

A device for suturing a vascular puncture site includes a shaft having a distal end terminating in a pair of resilient prongs, each of which releasably carries a suture anchor attached to one end of a suture. The shaft is installed within a hollow tube for longitudinal translation therein between first and second positions. The tube has a distal end portion and an opening spaced proximally therefrom. When the shaft is in its first position, the prongs are radially closed in the distal end portion. When the shaft is in its second position, the prongs expand radially to an open position through the opening. The proximal end of the shaft is connected to an actuation member in a fitting that is removably connectable to the proximal end of a sheath. The distal end of the tube is introduced into the puncture site through the sheath, with the shaft in its first position. The sheath is partially withdrawn, leaving the distal end of the tube inside the vessel. The shaft is moved to its second position, whereupon the prongs expand to their open position, thus positioning the suture anchors for penetration of the vascular wall tissue by manipulation of the shaft and/or the tube. The shaft is moved back to its first position to retract the prongs back into the tube, leaving the suture anchors secured to the vascular wall tissue. The tube is withdrawn, leaving the sutures trailing from the anchors so as to be secured together.

20 Claims, 4 Drawing Sheets

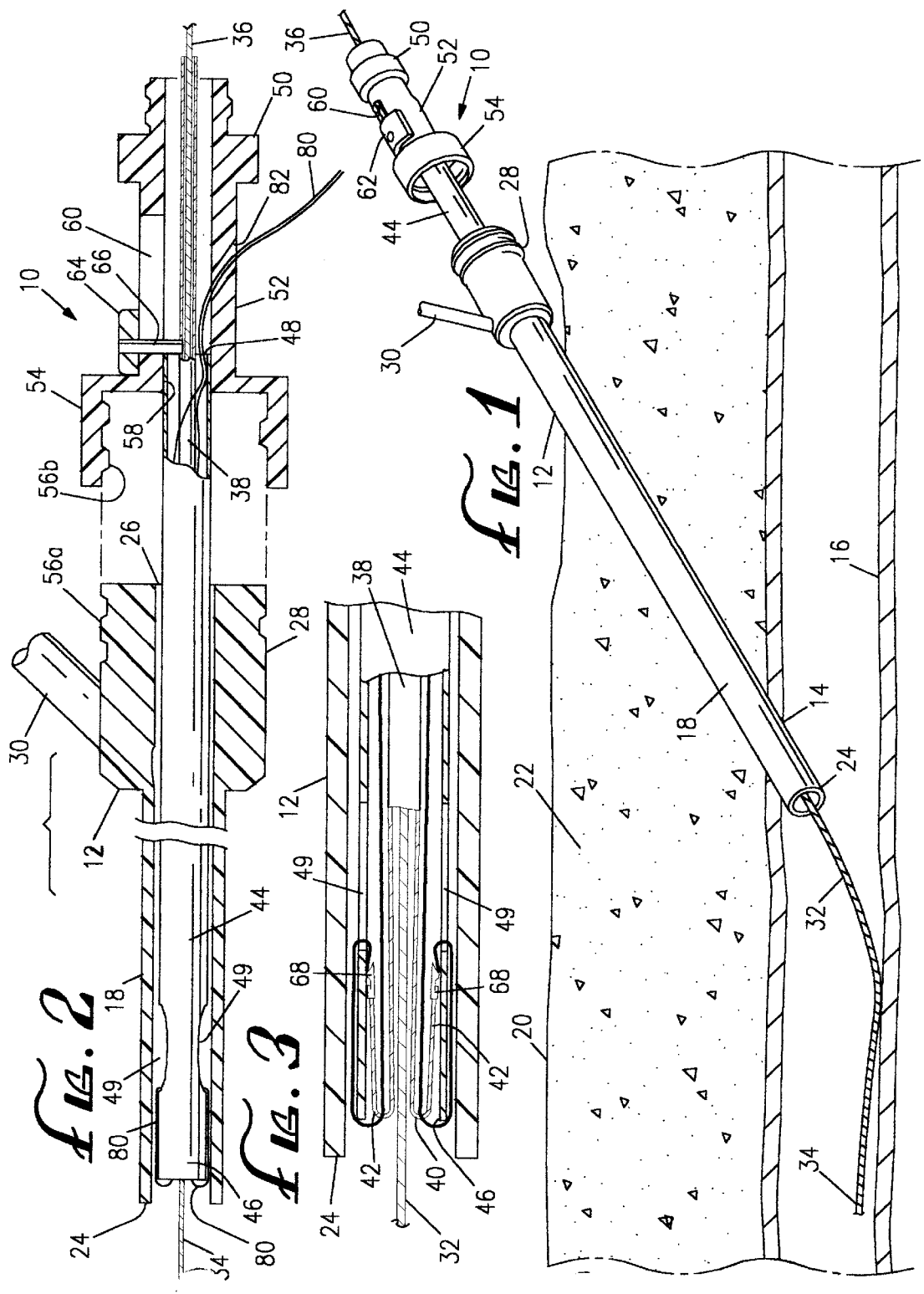

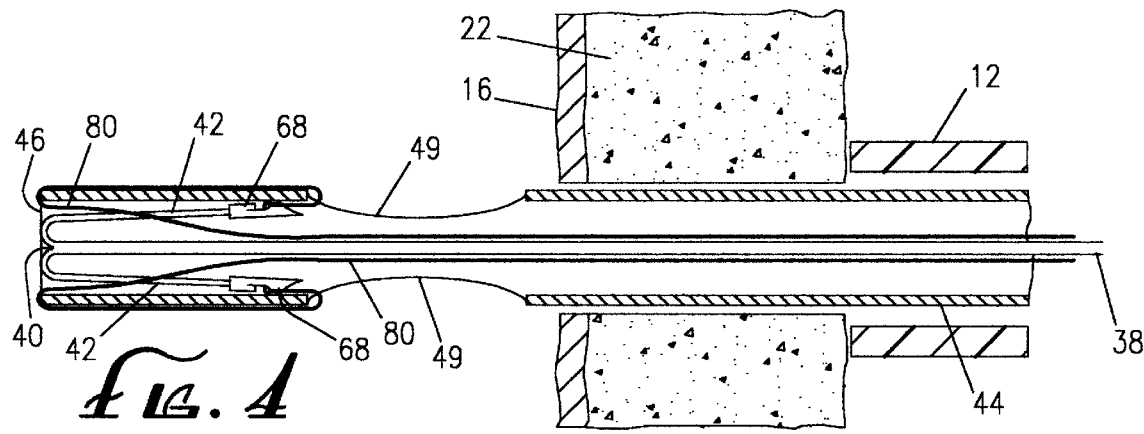
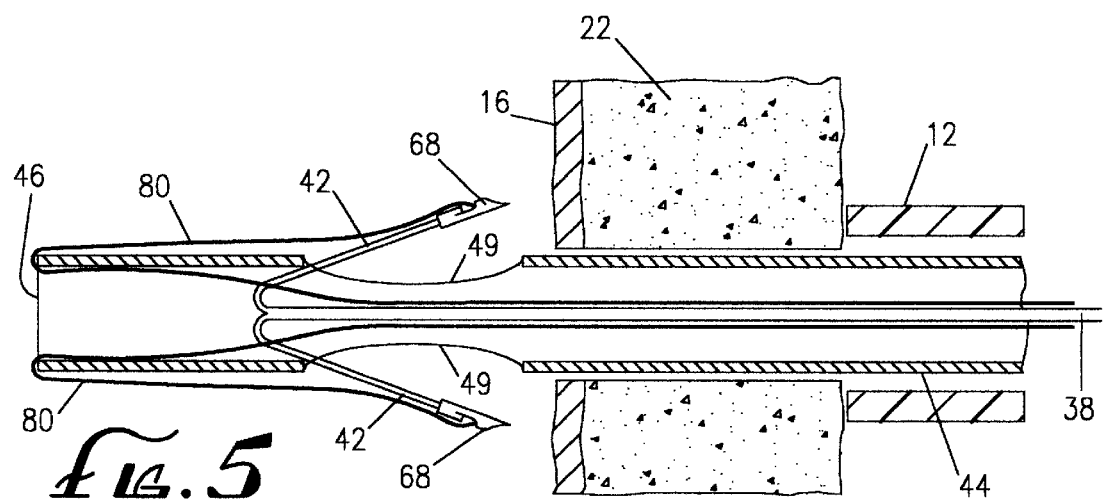
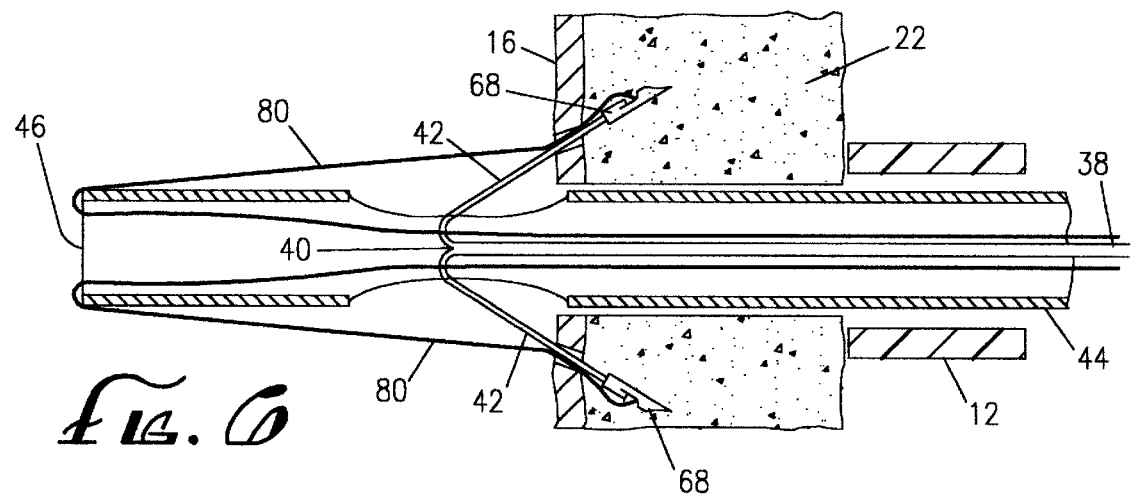

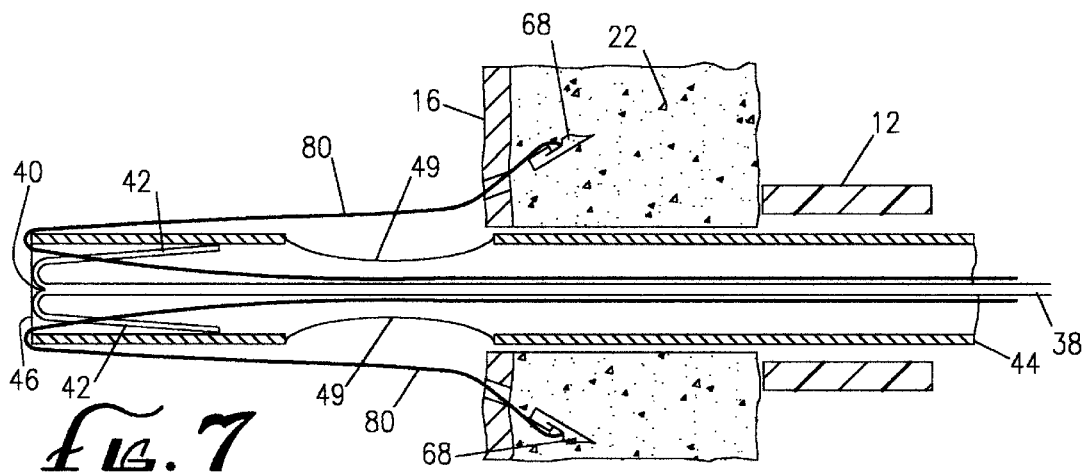
fig. 7
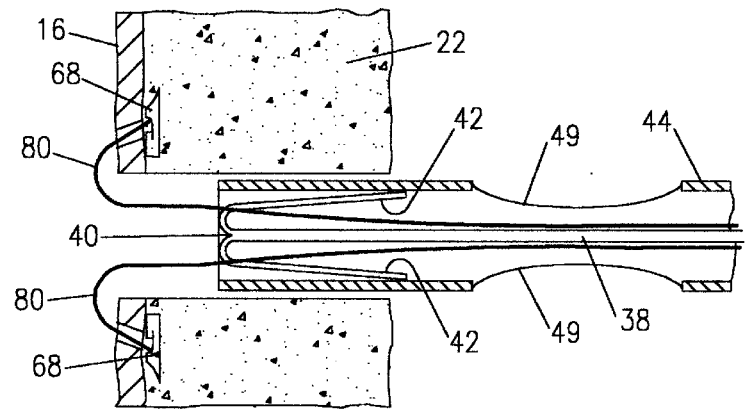
fig. 8
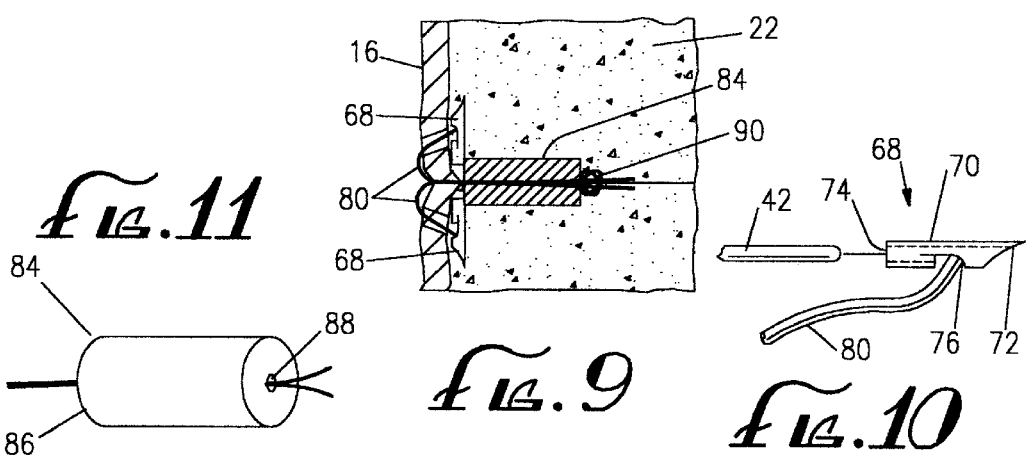
fig. 11
fig. 9
fig. 10

PERCUTANEOUS HEMOSTATIC SUTURING DEVICE AND METHOD

BACKGROUND OF THE INVENTION

This invention relates to the field of hemostasis devices; that is, medical instruments designed to stanch the flow of blood from a ruptured or punctured blood vessel. More specifically, in one aspect, the present invention relates to a percutaneous hemostasis device, i.e., a device that can reach through the skin and subcutaneous tissue to promote hemostasis in a perforated or punctured bodily lumen, such as a blood vessel. In another aspect, the present invention relates to the method of using such a device to promote hemostasis at a perforation or puncture site in a subcutaneous bodily lumen, particularly a blood vessel.

A growing number of therapeutic and diagnostic medical procedures involve the percutaneous introduction of instrumentation into a vein or artery. For example, percutaneous transluminal coronary angioplasty (PTCA), most often involving the femoral artery, is performed hundreds of thousands of times annually, while other vessel-piercing procedures (e.g., percutaneous coronary or peripheral angiography) number more than five million per year.

In each event, the closing and subsequent healing of the resultant vascular puncture is critical to the successful completion of the procedure. Traditionally, the application of external pressure to the skin entry site has been employed to stem bleeding from the wound until clotting and tissue rebuilding have sealed the perforation. (See, for example, U.S. Pat. No. 5,342,388—Toller, which discloses an external pressure application device for effecting hemostasis in a femoral artery puncture.) In some situations, this pressure must be maintained for up to an hour or more, during which the patient is immobilized, often with sandbags or the like. With externally-applied manual pressure, both patient comfort and practitioner efficiency are impaired. Additionally, a risk of hematoma exists, since bleeding from the vessel may continue until sufficient clotting effects hemostasis. Also, external pressure application devices may be unsuitable for obese patients, since the skin surface may be a considerable distance from the vascular puncture site, thereby rendering skin compression inaccurate and thus less effective.

Consequently, devices have been developed for promoting hemostasis directly at the site of the vascular perforation. For example, there are devices that deploy intraluminal plugs within the vessel to close the puncture site, as disclosed in the following U.S. Pat. Nos.; 4,852,568—Kensey; 4,890,612—Kensey; 5,021,059—Kensey et al.; and 5,061,274—Kensey. Another approach is to deliver a tissue adhesive or clotting agent to the perforation site, as disclosed in the following U.S. Pat. Nos.: 5,221,259—Weldon et al.; 5,383,899—Hammerslag; 5,419,765—Weldon et al.; and 5,486,195—Myers et al. This method may entail some risk of disadvantageously introducing some of the adhesive or clotting agent into the bloodstream. Still another approach is the application of pressure directly to the perforation site, as exemplified by PCT International Publication Number WO 95/32671; U.S. Pat. No. 4,619,261—Guerrieo; and U.S. Pat. No. 4,929,246—Sinofsky, the last-named disclosing the simultaneous application of direct pressure to the perforated vessel and the direction of laser energy through an optical fiber to cauterize the wound. Yet another approach is disclosed in U.S. Pat. No. 5,275,616—Fowler, wherein a cylindrical plug is inserted along the shaft of a catheter segment extending from the skin surface to the blood vessel. The catheter is then removed so that the plug can expand as fluid is drawn into the plug from the vessel and the surrounding tissue. Unless pressure is applied, however, bleeding may occur around the plug into the subcutaneous tissue. A similar concept is disclosed in U.S. Pat. No. 5,391,183—Janzen et al., which discloses a variety of plug delivery devices, including threaded plug pushers and multilegged channels, that install a plug that may be resorbable.

Many of the above-noted devices rely, to varying degrees, on tactile sensation alone to indicate to the surgeon the proper placement of the puncture closing instrumentation, and they may also require upstream clamping of the blood vessel to reduce intraluminal pressure to approximately atmospheric pressure at the puncture site.

Another type of percutaneous vascular hemostasis device is exemplified in U.S. Pat. Nos. 5,417,699 and 5,527,322, both to Klein et al.; U.S. Pat. No. 5,462,561—Voda; and U.S. Pat. No. 5,364,408—Gordon. This type of device comprises a mechanism for delivering a suture percutaneously to a vascular suturing site, and then tying the suture in situ. While such devices, if properly employed, are capable of very effectively stemming blood flow, they may require a relatively high degree of dexterity to be operated properly. Furthermore, they tend to be somewhat complex and expensive to manufacture, and thus are not practically employed as single use, disposable products. Consequently, sterilization may be required between uses to reduce the risk of infection, thereby increasing their cost and inconvenience.

Accordingly, there has been a long-felt need for an effective percutaneous vascular hemostasis device that is relatively simple and inexpensive to manufacture and easy to use, that is adapted for use as disposable device, and that does not require the introduction of a foreign substance—such as a plug, tissue adhesive, or clotting agent—into the bloodstream.

SUMMARY OF THE INVENTION

Broadly, the present invention is a percutaneous hemostatic suturing device for the suturing of a vascular puncture site or the like, wherein the device comprises a shaft having a distal end terminating in a pair of resilient prongs, each of which releasably carries a "toggle"-like suture anchor attached to one end of a length of suture material and having a sharpened tip. The shaft is installed axially within a hollow tube for longitudinal translation therein between a first position and a second position. The tube has a distal end portion and an opening spaced a short distance proximally from its distal end portion. When the shaft is in its first position, the prongs are retained in a radially closed position by the distal end portion of the tube. When the shaft is in its second position, the prongs are aligned with the opening and are thereby released to spring resiliently radially outwardly from the axis of the tube through the opening.

The proximal end of the shaft is connected to an actuation member installed in a fitting that is removably connectable to the proximal end of an introducer sheath. The actuation member may be, for example, a button that is movable between a first position, corresponding to the first position of the shaft, and a second position, corresponding to the second position of the shaft.

The distal end of the tube is introduced into the puncture site in the vascular wall tissue through the sheath, with the shaft in its first position. The sheath is partially withdrawn in the proximal direction, leaving the distal end of the tube exposed inside the vessel, with the shaft in its first position. The shaft is then moved proximally to its second position, whereupon the prongs, being aligned with the opening in the tube, expand radially outwardly, pointing toward the proximal end of the tube and the interior of the vascular wall, and thus positioning the suture anchors for subsequent penetration of the vascular wall tissue. The shaft and/or the tube is then manipulated so as to cause the suture anchors to penetrate the vascular wall tissue on opposite sides of the tube, until they are located outside the vascular wall. The shaft is pushed distally back to its first position to retract the prongs back into their closed position in the distal end portion of the tube. This retraction of the prongs to their closed position releases the suture anchors from the prongs, leaving the suture anchors secured to the tissue on the outside of the vascular wall. Finally, the tube is withdrawn in the proximal direction from the puncture site, leaving the sutures trailing from each of the anchors. A closure sleeve is advanced over the sutures to the outside of the vessel wall, and the opposite (free) ends of the sutures are tied or otherwise secured together.

As will be appreciated from the detailed description that follows, the present invention provides a secure closure of the puncture site, thus promoting effective hemostasis. Furthermore, the present invention commends itself to the use of conventional sutures, e.g., those of the self-dissolving type, rather than the introduction of foreign agents in the bloodstream. In addition, the apparatus of the present invention is simple to use, and it lends itself to economical manufacture, thus allowing it to be embodied in a disposable implement.

BRIEF DESCRIPTION OF THE DRAWINGS

FIG. 1 is a perspective view of a surgical assembly comprising a percutaneous hemostatic suturing device in accordance with a preferred embodiment of the present invention contained within a sheath positioned within a vascular puncture site through a patient's skin and subcutaneous tissue, showing the actuation mechanism of the present invention;

FIG. 2 is an axial cross-sectional view of the assembly of FIG. 1, showing the sheath and the actuation mechanism in axial cross section and the tube of the present invention in elevation, partially broken away to reveal the proximal end of the shaft;

FIG. 3 shows the proximal end of the present invention in an axial cross-sectional view, prior to the deployment of the suture-carrying toggles;

FIGS. 4 through 9 are axial cross-sectional views, similar to that of FIG. 3, showing the steps in the deployment of the toggles;

FIG. 10 is an elevational view of a toggle of the type employed in a preferred embodiment of the present invention;

FIG. 11 is a perspective view of a suture closure sleeve, as used in the step illustrated in FIG. 9;

DETAILED DESCRIPTION OF THE INVENTION

Figure 12:
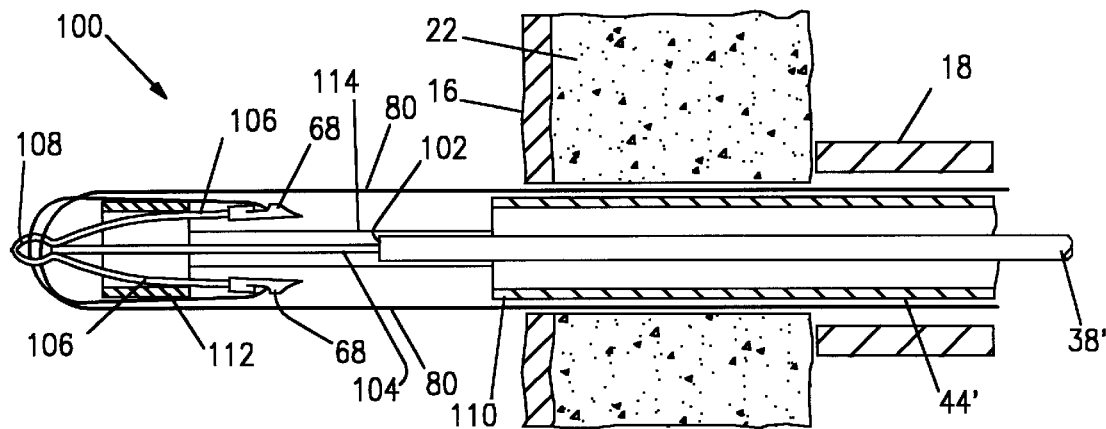
FIG. 12 is an axial cross-sectional view of a percutaneous hemostatic suturing device in accordance with an alternative embodiment of the invention in an operational position analogous to that shown in FIG. 4.

Referring first to FIGS. 1, 2, and 3, a percutaneous hemostatic suturing device 10, in accordance with a preferred embodiment of the present invention, is shown disposed within an introducer sheath 12 prior to deployment of the device 10 at a perforation or puncture site 14 in a subcutaneous bodily lumen 16. For the purposes of the ensuing discussion, the lumen 16 will be referred to below as a blood vessel, although the adaptation of the present invention for use in procedures involving other organs will readily suggest itself to those skilled in the pertinent arts.

The sheath 12 is may be a conventional catheter sheath, commonly used in the above-mentioned interventional procedures, and, as shown in FIG. 1, it is positioned as it would be after the completion of such a surgical procedure. Specifically, the sheath 12 comprises an elongate hollow tube or barrel 18 that is inserted through the skin 20 and subcutaneous tissue 22, with an open internal or distal end 24 that has been inserted into the vessel 16 through the puncture site 14. The barrel 18 has an open external or proximal end 26 that extends from a surgical entry site in the skin 20, and that is formed into an enlarged-diameter fitting 28. The fitting 28 includes a port 30 that communicates with the interior of the trocar barrel 18, and that serves as a conduit for the introduction of a contrasting agent, of the type commonly used in many angiographic procedures.

FIG. 1 shows the sheath 12 after the completion of the procedure. A guide wire 32, which may optionally be used to guide instruments such as catheters down the sheath 12, has been left in place, threaded through the barrel 18, with a first or internal end 34 extending through the distal end 24 of the barrel 18 so as to be disposed within the vessel 16, and a second or external end 36 that extends out of the proximal end 26 of the barrel 18.

The hemostatic suturing device 10 comprises an elongate, hollow, tubular shaft 38 having a main body portion and a distal end portion 40 that terminates in a pair of resilient prongs 42, as will be described in detail below. The inside diameter of the shaft 38 is large enough to allow the guide wire 32 to be freely threaded through it. The shaft 38 is disposed for longitudinal translation within a coaxial tube 44, the outside diameter of which is slightly less than the inside diameter of the sheath barrel 18, so that there is a coaxial clearance space between the tube 44 and the barrel 18. As will be explained below, the shaft 38 is longitudinally movable within the tube 44 between a first (distal) position and a second (proximal) position. The tube 44 has an open distal end 46 dimensioned to be received in the vessel through the puncture site 14, and an open proximal end 48, with a pair of openings 49 located a short distance proximally from the distal end 46. The openings 49 are located so as to have an angular separation from each other of between about 120° and about 180°.

A handle assembly 50 is attached to the proximal end 48 of the tube 44. The handle assembly 50 includes a hollow, tubular central portion 52 and a distal end portion formed as a cup-like hub 54, sized to mate with the sheath fitting 28. The hub 54 is removably attachable to the fitting 28, either by a friction fit, or by the use of mating threads 56a, 56b, as shown. The hub 54 has a central bore 58 that receives the proximal end 48 of the tube 44, and that communicates with the interior of the central portion 52. The shaft 38 has a proximal end portion that extends proximally from the proximal end 48 of the tube 44 and through the interior of the central portion 52 of the handle assembly, as best shown in FIG. 2.

The central portion 52 of the handle assembly 50 has an axial slot 60 that communicates with its interior. An actuation member 62 is slidable along the slot 60, and includes a thumb button 64 attached to one end of a stem 66 that rides in the slot 60. The other end of the stem is fixed to the proximal end portion of the shaft 38. Movement of the actuation member 62 in the slot 60 thus causes the shaft 38 to move axially within and with respect to the tube 44, as explained below.

Each of the prongs 42 at the distal end of the shaft 38 releasably carries a toggle-like suture anchor 68. The structure of the suture anchor 68 is best shown in FIG. 10. Each suture anchor 68 comprises a short, hollow, tubular body 70 with a sharpened distal end 72 and an open proximal end 74 that receives the associated prong 42 with a friction fit. The distal end 72 is configured to facilitate the penetration of the vascular wall tissue by the suture anchor 68, as will be explained below. The tubular body 70 has a side opening 76 that receives a fixed end of a length of suture 80. The fixed end of the suture 80 is attached to the interior of the tubular body 70, preferably by a mechanical crimp, or by a suitable biocompatible adhesive. The tubular body 70 fits onto its associated prong 42 with a slip fit, and the suture anchor 68 is retained on its associated prong 42 by tension on the suture 80. Releasing this tension allows the suture anchor 68 to be removed from the prong 42 with a light force in the distal direction, as will be described below.

As shown in FIGS. 2 and 3, prior to the deployment of the device 10, the prongs 42 are retained in a radially collapsed or closed position by the distal end 46 of the tube 44. In this closed position, the prongs 42 extend proximally toward the openings 49. The sutures 80 extend from the suture anchors 68, out through the openings 49, then along the outside of the tube 44, and into the tube 44 through the open distal end 46 thereof. As shown in FIG. 2, the sutures then extend proximally through the interior of the tube 44, emerging through the proximal end 48 of the tube 44, and into the handle assembly 50. The free ends of the sutures 80 then pass through an aperture 82 in the handle assembly 50.

The operation of the device 10 can now be described. FIG. 1 shows the device 10 and the sheath 12 prior to deployment of the device 10. The distal end 46 of the tube 44 is introduced into the puncture site 14 in the vascular wall 16 through the sheath 12, with the handle assembly 50 displaced proximally from the fitting 28 at the proximal end 26 of the sheath 12. As shown in FIG. 3, the shaft 38 is in a first longitudinal position relative to the tube 44. In this first position, the distal end portion 40 of the shaft 38 is contained within the distal end 46 of the tube 44, whereby the prongs 42 are retained in the above-described closed position in the distal end 46 of the tube 44.

As shown in FIG. 4, the sheath 12 is partially withdrawn in the proximal direction, leaving the distal end 46 of the tube 44 exposed inside the vessel 16, with the shaft 38 still in its first position. The shaft 38 is then moved proximally to a second longitudinal position relative to the tube 44, as shown in FIG. 5, in which the prongs 42 come into alignment with the openings 49 in the tube 44. The prongs 42 resiliently expand radially outwardly from the openings 49 to an open position, in which they point toward the proximal end 48 of the tube 44 and the interior of the vascular wall 16. The suture anchors 68 are thus positioned for the penetration of the vascular wall tissue in the next step.

Next, as shown in FIG. 6, practitioner manipulates the tube 44 and/or the shaft 38 so as to cause the suture anchors 68 to penetrate the vascular wall 16 on roughly opposite sides of the tube 44, until they are located outside the vascular wall 16. This manipulation may include pulling the tube 44 and/or the shaft 38 a short distance in the proximal direction. Then, as shown in FIG. 7, the shaft 38 is pushed distally back to its first position to retract the prongs 42 back into their closed position in the tube 44, thereby stripping the suture anchors 68 from the prongs, and leaving the suture anchors 68 secured to the outside surface of the vascular wall 16. As shown in FIG. 8, the tube 44 is withdrawn in the proximal direction from the puncture site, leaving the sutures 80 trailing from each of the suture anchors 68. The free ends of the sutures 80 can then be tied together to conclude the procedure. Preferably, the sutures 80 are of the resorbable type, well known in the surgical arts, that dissolve over time into the bodily tissue.

To facilitate the closure of the puncture site and the tying of the suture ends, a closure sleeve 84, illustrated in FIG. 11, may optionally be employed. The closure sleeve 84 comprises a cylindrical body 86 with an axial passage 88 therethrough. The diameter of the passage 88 is sufficient to allow both sutures 80 to be easily passed through it. The sleeve 84 may be from about 3 mm to about 15 mm in length, with an outside diameter of about 2 mm to about 6 mm, the dimensions depending on the requirements of the procedure involved and the desires of the physician.

The sleeve 84 is formed of a biocompatible material, preferably one that harmlessly dissolves over time in the body tissue. Suitable dissolvable materials include a number of well-known bioresorbable polymers, methyl cellulose, carbowaxes, carboxymethyl cellulose, and gelatin (preferably pigskin gelatin). Among the suitable bioresorbable polymers are polylactic glycolic acids, polyvinyl pyrrolidone, polyvinyl alcohol, polyproline, and polyethylene oxide. Alternatively, the sleeve 84 may be made of a non-degradable material, such as a metal (preferably stainless steel) or a non-resorbable polymer.

FIG. 9 illustrates the use of the closure sleeve 84. The closure sleeve 84 is advanced down over the sutures 80 to the puncture site. As it advances, the closure sleeve 84 gathers the tissue together around the puncture site, and provides a degree of external compression on the adjacent tissue. The closure sleeve 84 nevertheless remains outside the bloodstream. The free ends of the sutures 80 can then be tied together in a knot 90 on the proximal side of the closure sleeve 84. Alternatively, if there is sufficient frictional engagement between the closure sleeve and the sutures, the frictional engagement alone may be sufficient to secure the sutures together, without the need for a knot.

Figure 13:
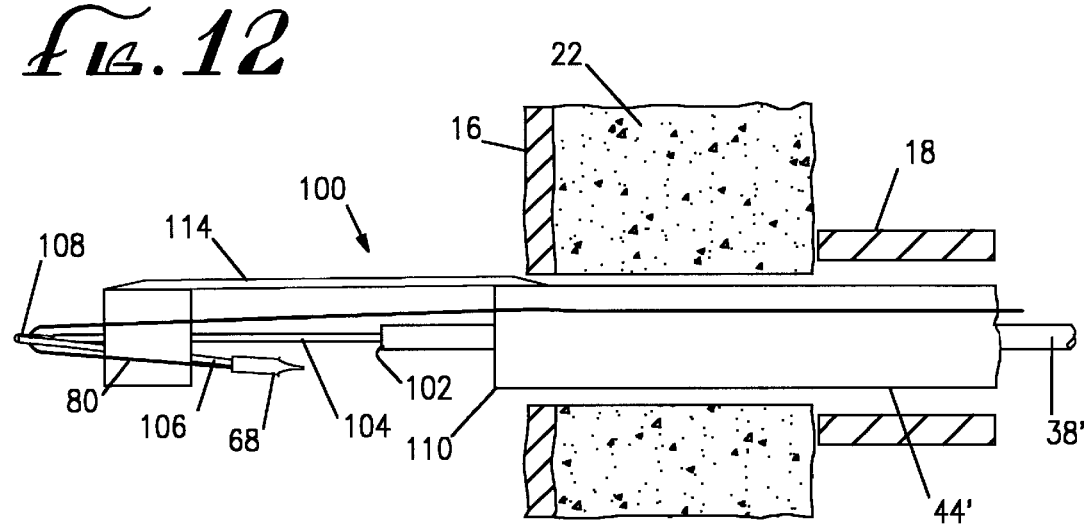
FIG. 13 is an elevational view of the device of FIG. 12, with the device rotated 90 degrees about its axis from the view of FIG. 12.
Figure 14:
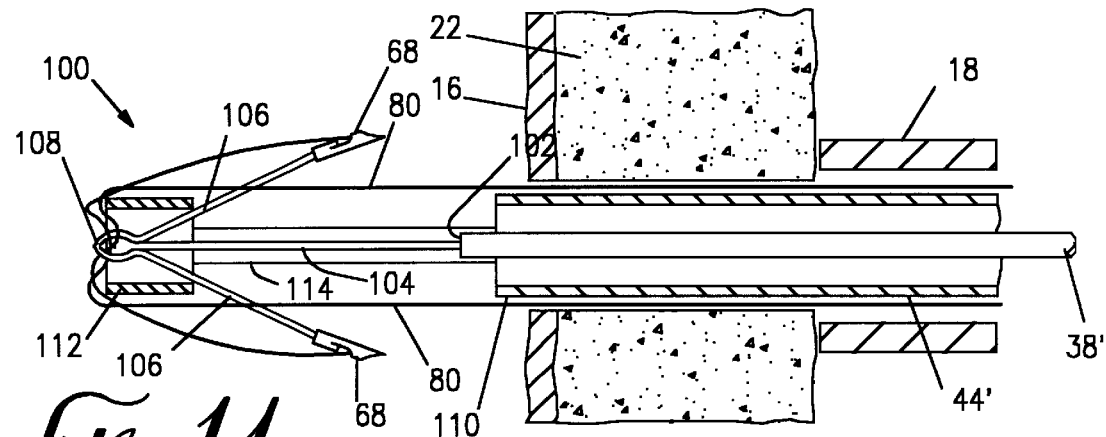
FIG. 14 is an axial cross-sectional view of the device of FIG. 12, in an operational position analogous to that shown in FIG. 5.

FIGS. 12, 13 and 14 illustrate a percutaneous hemostatic suturing device 100 in accordance with an alternative embodiment of the invention. This embodiment differs from the above-described preferred embodiment only in the structure of the distal portions of the shaft and the tube; in all other respects, the two embodiments are the same.

In the embodiment of FIGS. 12, 13 and 14, the device 100 comprises an elongate, hollow, tubular shaft 38' that terminates in an open distal end 102. Fixed to the distal shaft end 102, and extending distally therefrom, is a prong support wire 104. Fixed to the distal end of the prong support wire 104 is a pair of resilient prongs 106, joined together distally from the distal end of the strut 104 so as to form an eyelet 108. The inside diameter of the shaft 38' is large enough to allow a guide wire (not shown) to be freely threaded through it. The shaft 38' is disposed for longitudinal translation within a coaxial tube 44', the outside diameter of which is slightly less than the inside diameter of the sheath barrel 18, so that there is a coaxial clearance space between the tube 44' and the barrel 18. As in the above-described preferred embodiment, the shaft 38' is longitudinally movable within the tube 44' between a first (distal) position and a second (proximal) position.

In the device 100, the tube 44' includes a main portion 110 and an open distal end collar 112. The main tube portion 110 terminates a short distance proximally from the distal end 102 of the shaft 38', and it is connected to the end collar 112 by an axial strut 114. Both the main tube portion 110 and the end collar 112 are dimensioned to be received in the vessel through the puncture site 14. The separation between the main tube portion 110 and the end collar 112 creates an opening in the tube 44' into which the ends of the prongs 106 extend.

As in the above-described preferred embodiment, each of the prongs 106 releasably carries a suture anchor 68, to which is attached a length of suture 80, as described above. As shown in FIGS. 12 and 13, prior to the deployment of the device 100, the prongs 106 are collapsed inside the distal end collar 112 of the tube 44', extending proximally toward the tube opening. The sutures 80 extend from the suture anchors 68, distally over the end collar 112, through the eyelet 108, back over the end collar 112, and then proximally past the tube opening and along the outside of the main tube portion 110. As in the previously-described embodiment, as shown in FIG. 2, the sutures then extend proximally through the interior of the tube 44', emerging through the proximal end 48 of the tube 44', and into the handle assembly 50. The free ends of the sutures 80 then pass through an aperture 82 in the handle assembly 50.

The operation of the embodiment of FIGS. 12, 13 and 14 is similar to the operation of the preferred embodiment. The distal end collar 112 of the tube 44' is introduced into the puncture site 14 in the vascular wall 16 through the sheath 12, with the handle assembly 50 displaced proximally from the fitting 28 at the proximal end 26 of the sheath 12. As shown in FIGS. 12 and 13, the shaft 38' is in a first longitudinal position relative to the tube 44'. In this first position, the prong support wire 104 at distal end of the shaft 38' is partially contained within the distal end collar 112 of the tube 44', whereby the prongs 106 are retained in a radially collapsed or closed position by the distal end collar 112. In this closed position, the prongs 106 extend toward the opening, as described above.

The sheath 12 is partially withdrawn in the proximal direction, leaving the distal end collar 112 of the tube 44' exposed inside the vessel 16, with the shaft 38' still in its first position. As shown in FIG. 14, the shaft 38' is then moved proximally to a second longitudinal position relative to the tube 44', moving the prongs 106 into the tube opening. The prongs 106 resiliently expand radially outwardly from the opening to an open position, in which they point toward the proximal end 48 of the tube 44 and the interior of the vascular wall 16, as described above with respect to the preferred embodiment. The suture anchors 68 are thus positioned for the penetration of the vascular wall tissue in the next step. Thereafter, the operation of the device 100 is in accordance with the operational description set forth above in connection with FIGS. 6 through 11.

As will be appreciated from the foregoing description, the present invention provides a secure closure of the puncture site, thus promoting effective hemostasis, using conventional sutures, without introducing foreign agents in the bloodstream. In addition, the apparatus of the present invention is simple to use and economical to manufacture, thus allowing it to be disposable.

While preferred and alternative embodiments of the invention has been described herein, a number of variations and modifications may suggest themselves to those skilled in the pertinent arts. For example, the number and arrangement of the prongs that install the suture anchors may vary, as well as the configuration of the suture anchors themselves. These and other variations and modifications that may suggest themselves are considered within the spirit and scope of the invention, as defined in the claims that follow.

What is claimed is:

1. A percutaneous suturing device for suturing a puncture site in the tissue of a bodily lumen, the device comprising:
   a hollow tube having a distal end portion dimensioned to enter the lumen through the puncture site, and an opening located proximally from the distal end portion;
   a shaft having a distal end portion terminating in a resilient prong, the shaft being disposed within the tube for longitudinal translation therein between a first position in which the prong is retained in a radially closed position by the distal end portion of the tube, and a second position in which the prong is resiliently expanded radially outwardly to an open position through the opening;
   a suture anchor releasably retained on the prong and configured for the penetration of the lumen tissue adjacent the puncture site;
   a length of suture attached to the suture anchor; and
   an actuation member operably connected to the shaft, the actuation member being actuable to move the shaft from the first position to the second position;
   whereby the movement of the prong to the open position in response to the movement of the shaft from the first position to the second position, when the distal end portion of the tube is entered into the vessel, positions the suture anchor to penetrate the lumen tissue adjacent the puncture site, and whereby the subsequent movement of the shaft from the second position to the first position after the suture anchor has penetrated the lumen tissue releases the prong from the suture anchor and contracts the prong radially into the closed position at least partially within the distal end portion of the tube, thereby leaving the suture anchor secured to the lumen tissue with the suture attached to the suture anchor in a position to be secured so as to close the puncture site.

2. The device of claim 1, wherein the tube includes a pair of side openings, wherein the distal end portion of the shaft terminates in a pair of resilient prongs, wherein a suture anchor configured for the penetration of lumen tissue and having a length of suture attached to it is releasably retained on each of the prongs, and wherein, when the shaft is in the second position, each of the prongs is aligned with one of the side openings so that each of the prongs expands radially through its associated side opening to the expanded position.

3. The device of claim 2, wherein the shaft has a proximal end portion, and wherein the actuation member is operably connected to the proximal end portion of the shaft.

4. The device of claim 2, wherein the suture anchor comprises a tubular body having an open end dimensioned to receive the prong, and a pointed end configured for the penetration of lumen tissue.

5. The device of claim 3, wherein the suture anchor comprises a tubular body having an open end dimensioned to receive the prong, and a pointed end configured for the penetration of lumen tissue.

6. The device of claim 1, wherein the tube is dimensioned to be received in a catheter sheath.

7. The device of claim 1, wherein the shaft has a proximal end portion, and wherein the actuation member is operably connected to the proximal end portion of the shaft.

8. The device of claim 7, wherein the suture anchor comprises a tubular body having an open end dimensioned to receive the prong, and a pointed end configured for the penetration of lumen tissue.

9. The device of claim 1, wherein the suture anchor comprises a tubular body having an open end dimensioned to receive the prong, and a pointed end configured for the penetration of lumen tissue.

10. A percutaneous suturing device for suturing a puncture site in the tissue of a bodily lumen, the device comprising:

a hollow tube having a distal end portion dimensioned to enter the lumen through the puncture site, and a pair of side openings longitudinally spaced from the distal end portion;

a shaft disposed within the tube for longitudinal translation therein between a first position and a second position;

a pair of suture anchors configured for the penetration of lumen tissue adjacent the puncture site;

a length of suture attached to each of the suture anchors;

first means, on the shaft, for releasably retaining the suture anchors on the shaft, the first means being aligned with the side openings when the shaft is in the second position; and second means, operably connected to the shaft, for moving the shaft between the first position and the second position, wherein the movement of the shaft from the first position to the second position exposes the first means through the side openings and positions the suture anchors for penetration into the lumen tissue, and wherein the movement of the shaft from the second position to the first position, after the penetration of the lumen tissue by the suture anchors, releases the suture anchors from the first means, leaving the suture anchors secured to the lumen tissue with the lengths of suture positioned to be secured so as to close the puncture site.

11. The device of claim 10, wherein the tube is dimensioned to be received in a catheter sheath.

12. The device of claim 10, wherein the shaft has a distal end, and wherein the first means comprises a pair of resilient prongs extending from the distal end of the shaft and positioned so that, when the shaft is in the first position, the prongs are retained in a radially closed position by the distal end portion of the tube, and when the shaft is in the second position, each of the prongs expands radially through one of the side openings to an open position in which the suture anchors are positioned to penetrate the lumen tissue adjacent the puncture site, and whereby the subsequent movement of the shaft from the second position to the first position after the suture anchors have penetrated the lumen tissue releases the prongs from their respective suture anchors and contracts the prongs radially into the closed position at least partially within the distal end portion of the tube, thereby leaving the suture anchors secured to the lumen tissue with the suture attached to the suture anchors in a position to be tied.

13. The device of claim 10, wherein the shaft has a proximal end portion, and wherein the actuation member is operably connected to the proximal end portion of the shaft.

14. The device of claim 12, wherein the shaft has a proximal end portion, and wherein the actuation member is operably connected to the proximal end portion of the shaft.

15. The device of claim 12, wherein each of the suture anchors comprises a tubular body having an open end dimensioned to receive one of the prongs, and a pointed end configured for the penetration of lumen tissue.

16. The device of claim 14, wherein each of the suture anchors comprises a tubular body having an open end dimensioned to receive one of the prongs, and a pointed end configured for the penetration of lumen tissue.

17. A method of percutaneously suturing a subcutaneous puncture site in a bodily lumen, comprising the steps of:

(a) providing a hollow tube having a distal end portion dimensioned to enter the lumen through the puncture site and an opening longitudinally spaced from the distal end portion, the tube containing a shaft having a pair of resilient prongs, each of which releasably retains a tissue-penetrable suture anchor to which is attached a length of suture, the shaft being axially movable relative to the tube between a first position in which the prongs are retained in a radially collapsed position within the distal end portion of the tube and a second position in which the prongs are expanded radially outwardly through the opening;

(b) with the shaft in the first position, introducing the distal end portion of the tube into the lumen through the puncture site;

(c) moving the shaft to the second position so as to release the prongs through the opening, thereby positioning the suture anchors for penetration of lumen tissue adjacent the puncture site;

(d) manipulating the shaft and/or the tube so that the suture anchors penetrate the lumen tissue adjacent the puncture site;

(e) moving the shaft to the first position so as to release the prongs from the suture anchors, while leaving the suture anchors secured to the lumen tissue; and (f) removing the tube and the shaft so as to leave the suture anchors secured to the lumen tissue with the lengths of suture positioned to be secured so as to close the puncture site.

18. The method of claim 17, further comprising the step of:

(g) tying the lengths of suture together so as to close the puncture site.

19. The method of claim 18, wherein the step of tying the lengths of sutures includes the steps of:

(g)(1) providing a closure sleeve comprising a tubular body with an axial passage through it;

(g)(2) passing the lengths of suture through the passage of the closure sleeve and advancing the closure sleeve along the lengths of suture toward the puncture site; and (g)(3) securing the ends of the lengths of suture together adjacent an end of the closure sleeve remote from the puncture site.

20. The method of claim 17, wherein the step of introducing the tube is performed through a catheter sheath.

* * * * *